United States Patent [19]
Dietz et al.

[11] Patent Number: 5,702,580
[45] Date of Patent: Dec. 30, 1997

[54] MEASURING SENSOR FOR DETERMINING THE OXYGEN CONTENT OF GAS MIXTURES

[75] Inventors: Hermann Dietz; Werner Gruenwald, both of Gerlingen; Claudio De La Prieta, Stuttgart; Gert Lindemann, Lichtenstein; Ulrich Eisele, Stuttgart; Carmen Schmiedel, Benningen, all of Germany

[73] Assignee: Robert Bosch GmbH, Stuttgart, Germany

[21] Appl. No.: 617,873

[22] PCT Filed: Sep. 22, 1995

[86] PCT No.: PCT/DE95/01305

§ 371 Date: Mar. 21, 1996

§ 102(e) Date: Mar. 21, 1996

[87] PCT Pub. No.: WO96/11394

PCT Pub. Date: Apr. 18, 1996

[30] Foreign Application Priority Data

Oct. 11, 1994 [DE] Germany .............. 44 36 222.6

[51] Int. Cl.$^6$ ................................ G01N 27/407
[52] U.S. Cl. ............... 204/426; 204/425; 204/429
[58] Field of Search ...................... 204/421–429

[56] References Cited

U.S. PATENT DOCUMENTS

| | | | |
|---|---|---|---|
| 4,250,010 | 2/1981 | Kondo et al. | 204/418 |
| 4,724,061 | 2/1988 | Nyberg | 204/426 |
| 4,765,880 | 8/1988 | Hayakawa et al. | 204/426 |
| 4,810,350 | 3/1989 | Mantese et al. | |

FOREIGN PATENT DOCUMENTS

| | | |
|---|---|---|
| 0580206 | 1/1994 | European Pat. Off. . |
| 3632456 | 4/1987 | Germany . |
| 4332487 | 3/1995 | Germany . |
| 2052758 | 1/1981 | United Kingdom . |

*Primary Examiner*—T. Tung
*Attorney, Agent, or Firm*—Spencer & Frank

[57] ABSTRACT

A measuring sensor for determining oxygen content in a gas mixture including exhaust gases of internal combustion engines, includes a base substrate which is comprised of a base material and which is electrically insulating; and an electrochemical measuring probe and an electrochemical reference probe arranged separate from each other on the base substrate. The measuring probe includes at least one internal electrode; at least one solid electrolyte island; and at least one external electrode. The measuring probe additionally includes a diffusion barrier. Further base material layers composed of the base material are provided so as to embed at least the diffusion barrier, the at least one internal electrodes for the measuring probe and the internal electrode for the reference probe. A diffusion hole is defined between the measuring probe and the reference probe which extends from the base substrate through the diffusion barrier and respective base material layers, and out to the gas mixture to be measured. Thermal stress and the accompanying tendency to cracking is reduced by providing the solid electrolyte as islands. Separate disposition of the measuring probe and the reference probe, i.e., without a common electrode, permits construction as individual layers using, for example, screen printing.

12 Claims, 2 Drawing Sheets

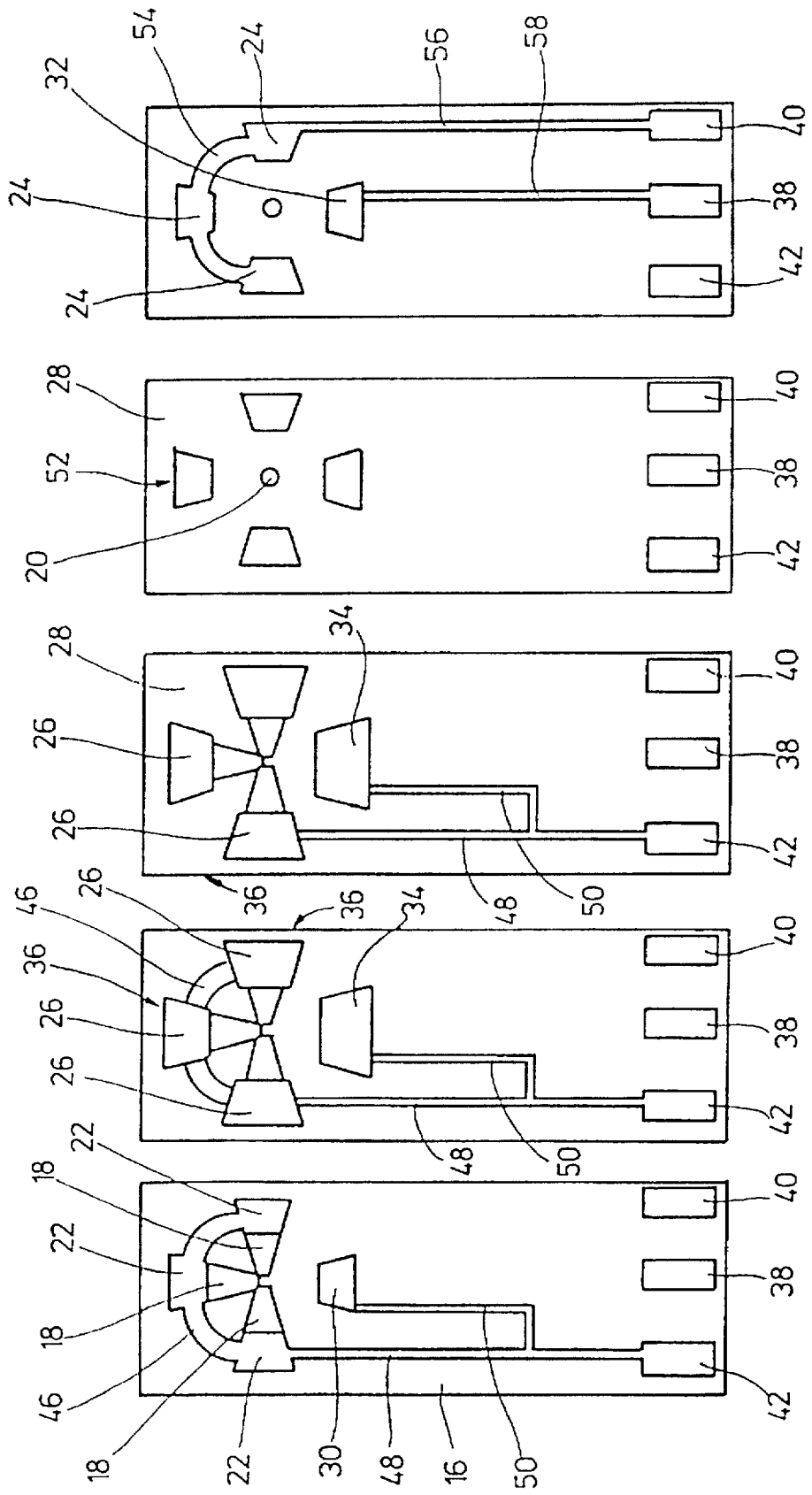

MEASURING SENSOR FOR DETERMINING THE OXYGEN CONTENT OF GAS MIXTURES

BACKGROUND OF THE INVENTION

1. Field of the Invention

The invention relates to a measuring sensor for determining the oxygen content in gas mixtures, in particular in exhaust gasses of internal combustion engines.

2. Background of the Related Art

Measuring sensors of this generic type are known. For example, DE-A1-36 32 456 discloses a probe for regulating the fuel-air mixture for internal combustion engines. This has a first pump cell with two porous electrodes, which are disposed on opposite sides of a first plate made of an oxygen ion conducting solid electrolyte, as well as a second pump cell which likewise has two porous electrodes, which in turn are disposed on opposite sides of a second plate made of an oxygen ion conducting solid electrolyte. Each porous electrode of the two pump cells contacts a gas chamber which is disposed between the pump cells and for its part communicates with the internal combustion engine exhaust gas to be measured via a conduit which functions as a diffusion limiting element. One of the porous electrodes of the first pump cell, namely the electrode which is not connected with the gas chamber, is simultaneously used as an internal standard oxygen reference. This electrode is connected via a leakage throttle element to the other electrode of the first pump cell, which communicates with the gas chamber. This disposition produces a measuring probe and reference probe which are each embodied as a pump cell.

By means of a measuring sensor of this kind, the composition of the exhaust gas of the internal combustion engine can be evaluated as to whether, in the fuel-air mixture with which the internal combustion engine is operated, fuel or oxygen are present in a stoichiometric surplus or whether the fuel and the air correspond to the stoichiometry. This is possible since the composition of the fuel-air mixture determines the composition of the exhaust gas in a known manner. In the so-called rich range—when there is a stoichiometric surplus of fuel—considerable quantities of unspent or partially burned fuel are found in the exhaust gas, while the oxygen component is relatively low. In the so-called lean range—when there is a stoichiometric preponderance of oxygen—the oxygen content in the exhaust gas is correspondingly high. In a stoichiometric composition of the fuel-air mixture, both fuel and oxygen are minimized in the exhaust gas. A common measure for the fuel-air ratio is the so-called lambda value measured in the exhaust gas, which is >1 in the lean range, <1 in the rich range and =1 in the exactly stoichiometric range. The lambda value can be determined by means of the measuring sensor mentioned at the beginning so that it is possible to control the fuel-air mixture for the internal combustion engine via an evaluation circuit connected to the measuring sensor.

The previous patent application DE 43 32 487 discloses a measuring sensor for determining the oxygen content of gas mixtures, in which a measuring probe and a reference probe are each embodied as a pump cell with a common electrode and are disposed in layers on a common substrate. The electrodes of the two pump cells are mutually enclosed by a solid electrolyte.

The known measuring sensors have in common that on the one hand, they are exposed to a high temperature exhaust gas of internal combustion engines, and on the other hand, require a minimum operating temperature for their use so that they often have an additional heat source. In this case, it is disadvantageous that, because of different heat expansion coefficients of the materials used, thermal stress occurs in the measuring sensors, which can lead to damage or destruction of the measuring sensor.

SUMMARY OF THE INVENTION

In contrast thereto, the measuring sensor according to the invention with the features mentioned in claim 1, has the advantage of having an improved thermal stress capability. Since the measuring probe and the reference probe are embedded separately in a common base substrate and the solid electrolytes are embodied by solid electrolyte islands, which are disposed exclusively in the region of the electrodes, the thermal stresses are reduced because of a different heat expansion coefficient of the solid electrolytes and the base material. As a particular result of the embodiment of the solid electrolytes as solid electrolyte islands, the absolute values of the heat-induced expansion differences between the solid electrolyte islands and the base substrate are minimized in such a way that no thermal stresses can occur and as a result no cracks occur in the measuring sensors.

Furthermore, as a result of the separate disposition of the measuring probe and the reference probe—that is, without a common electrode—it is possible to construct the measuring sensor preferably out of individual layers, in particular applied in accordance with the screen printing process. Because of a simple—because it is technologically known and controllable—construction of the layers, a measuring sensor can thus be produced which has a separate measuring probe and a separate reference probe. In this instance, the reference probe can be advantageously embodied as a lambda probe which determines the oxygen content of the gas mixture, while the measuring probe can be constructed as a limiting current pump cell with a different pump flow direction. The lambda probe is advantageously used here for setting the pump flow direction of the measuring probe, so that influence can be brought to bear on the composition of the measured gas mixture via a connected evaluation circuit, in particular via the setting of a fuel-air mixture for internal combustion engines.

Further advantageous embodiments of the invention ensue from the further features mentioned in the dependent claims.

BRIEF DESCRIPTION OF THE DRAWINGS

The invention will be explained in detail below in an exemplary embodiment in conjunction with the accompanying drawings. Shown are in:

FIGS. 3a to 3e, a layered construction of the measuring sensor.

DESCRIPTION OF THE PREFERRED EMBODIMENTS

Figure 1:
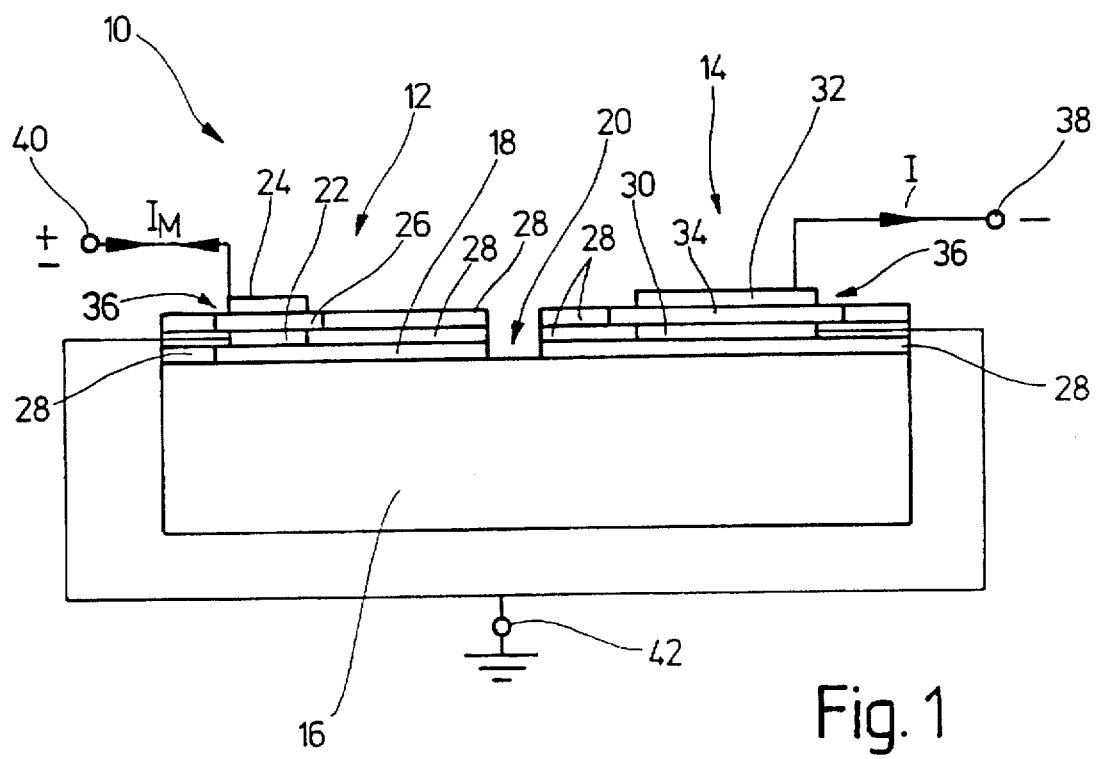
FIG. 1, a section through a measuring sensor.

FIG. 1 shows a measuring sensor, which is referred to in general by 10 and, used for determining the oxygen content in gas mixtures, in particular in exhaust gasses from internal combustion engines. The measuring sensor 10 is comprised of an electrochemical measuring probe 12 and an electrochemical reference probe 14. Both the measuring probe 12 and the reference probe 14 are constructed on a common base substrate 16. The base substrate 16 can for example be comprised of aluminum oxide $Al_2O_3$. A diffusion barrier 18 is mounted on the base substrate 16 and communicates via a diffusion hole 20 with the gas mixture to be measured. The diffusion barrier 18 is comprised for example of porous zirconium oxide. The measuring probe 12 is comprised of a first electrode 22 and a second electrode 24, between which a solid electrolyte 26 is disposed. In this case, the electrode 22 is disposed on the diffusion barrier 18, while the electrode 24 is exposed directly to the gas mixture to be measured. The electrodes 22 and 24 are porous and are comprised for example of platinum. The solid electrolyte 26 is comprised for example of zirconium oxide stabilized with yttrium oxide. The individual components of the measuring probe 12, that is, the diffusion barrier 18, the electrode 22, the solid electrolyte 26, and the electrode 24, are embedded in the base substrate 16, wherein the base substrate 16 is applied in individual layers 28 in the region of the measuring probe 12. In this case, —as will be explained in further detail in conjunction with FIG. 3—each of the layers 28 encompasses a part of the measuring probe 12. For reasons of clarity, an upper layer, which encompasses the electrode 24 so that it is still exposed to the exhaust gas, is not shown. The individual layers 28 are likewise comprised for example of aluminum oxide $Al_2O_3$. With regard to the exhaust gas to be measured, the electrode 22 is sealed off in a gas-tight manner by means of the solid electrolyte 26 and the overlapping layers 28.

The reference probe 14 is comprised of a first electrode 30 and a second electrode 32, between which a solid electrolyte 34 is disposed. The electrodes 30 and 32 in turn are comprised for example of porous platinum, while the solid electrolyte 34 is comprised for example of zirconium oxide stabilized with yttrium oxide. The electrodes 30 and 32 as well as the solid electrolyte 34 are likewise embedded again in the layers 28 of the base substrate 16. The first electrode 30 of the reference probe 14 is likewise sealed off in a gas-tight manner with regard to the gas mixture to be measured by means of the layers 28 and the solid electrolyte 34 and communicates with a reference gas, for example the atmosphere. The second electrode 32 of the reference probe 14 is exposed directly to the gas mixture to be measured.

As a whole, the measuring sensor 10 therefore consists of separately constructed measuring probes 12 and reference probes 14, which are, however, embedded in a common base substrate 16. The solid electrolytes 26 or 34 are disposed exclusively in the region of the electrodes 22 and 24 or 30 and 32, and are enclosed by the layers 28 of the base substrate 16 in the other regions of the measuring sensor 10. The solid electrolytes 26 or 34 consequently form solid electrolyte islands 36 (FIG. 3), which are disposed exclusively in the region of the electrodes 22 and 24 or 30 and 32. The electrodes 22, 24, 30, and 32 are connected via strip conductors, which are not shown in FIG. 1, to contact points which are guided outward and can be connected to an evaluation circuit. The electrode 32 is connected to a first contact point 38, the electrode 24 is connected to a second contact point 40, and the electrodes 22 and 30 are connected to a common third contact point 42.

Figure 2:
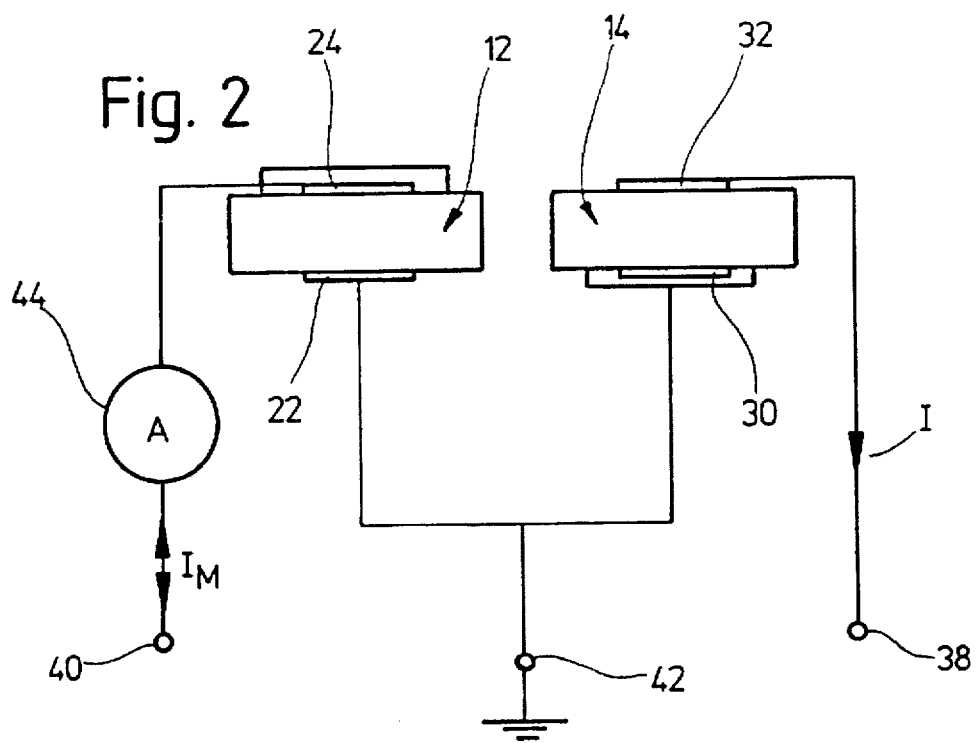
FIG. 2, an electrical equivalent circuit diagram of the measuring sensor.

FIG. 2 shows an electrical equivalent circuit diagram of the measuring sensor 10 shown in FIG. 1. It can be seen here that the measuring probe 12 and the reference probe 14 are elements which are connected to each other and separately constructed.

The measuring sensor 10 shown in FIGS. 1 and 2 performs the following functions:

Both the measuring probe 12 and the reference probe 14 are exposed to the gas mixture to be measured, for example the exhaust gas of an internal combustion engine. In this instance, the reference probe 14 functions as a generally known lambda probe. Here, a constant current I supplied by a current source, not shown, for example the battery of a motor vehicle, flows through the reference probe 14. If at this point an oxygen concentration changes between the electrodes 32 and 30 of the reference probe 14, for example because the fuel-air mixture with which the internal combustion engine, not shown, is operated is changed from the rich range into the lean range or vice versa, a detector voltage changes at the reference probe 14 and can be measured by the evaluation circuit, not shown. When there is a change into the rich range, that is when there is a lower oxygen concentration in the exhaust gas to be measured, the detector voltage decreases, while in the lean range it increases. The reference probe 14 consequently supplies a signal as to whether the internal combustion engine is operating with a rich or a lean mixture. The evaluation device, not shown, compares the detector voltage supplied by the reference probe 14 with a reference voltage and as a result of this supplies a measurement current $I_M$—in a manner not examined in detail here—, which contacts the measuring probe 12 via the contact point 40. The diffusion barrier 18 on the measuring probe 12 causes the measurement current $I_M$ in the measuring probe 12 to be determined exclusively by an oxygen ion diffusion process and a constant partial oxygen pressure can be maintained at the electrode 22. When operating in the lean range, that is, when there are oxygen rich exhaust gasses, the diffusion barrier 18 particularly impedes the diffusion of oxygen ions to the electrode 22; and when operating in the rich range, that is when there are exhaust gasses which are low in oxygen, the diffusion barrier 18 particularly impedes the diffusion of unspent portions of carbon monoxide and hydrogen to the electrode 22. The diffusion barrier 18 is constructed so that the partial oxygen pressure, which corresponds to the reference voltage, can occur at the electrode 22. The reference voltage is selected so that a particular partial oxygen pressure occurs when the lambda value of the exhaust gas =1, that is, operation is performed with a fuel-air mixture in the stoichiometric range. It is therefore assured that the measuring probe 12 functions as a limiting current probe 14 which is independent of the voltage. According to the lambda value of the exhaust gas, which is determined by means of the reference probe 14, the contact point 40 is connected as a cathode or anode for the measuring probe 12. When there is a lambda value >1, that is, in the lean range of the fuel-air mixture, the contact point 40 is connected as a cathode and when there is a lambda value <1, that is, in the rich range of the fuel-air mixture, the contact point 40 is connected as an anode. The measuring current $I_M$ which follows is determined via a measuring device 44, for example an ammeter. The direction and the intensity of the measuring current $I_M$ consequently produce a measurement for the oxygen content in the gas mixture to be measured, in particular in the exhaust gas of an internal combustion engine. The measuring current $I_M$ in this case is directly proportional to the oxygen content.

FIGS. 3a to 3e show the layered construction of the measuring sensor 10 wherein, beginning with FIG. 3a, the measuring sensor 10 is always shown with an additional layer in a top view. The parts which are the same as in FIGS. 1 and 2 are provided with the same reference numerals and are not explained again.

FIG. 3a shows a top view of the base substrate 16 on which the diffusion barrier 18 is disposed. In this case, the diffusion barrier 18 has segments which are disposed in a three-quarter circle around a center point, which later produces the diffusion hole 20. Here, the diffusion barrier segments 18 which are offset from one another by an angle of approximately 90° in a circular configuration. The first electrode 22 of the measuring probe 12 has segments and is disposed on respective diffusion barriers 18. The segments of electrode 22 are connected to one another via a strip conductor 46 which runs in an arc shape. The segments of electrode 22 are connected to the contact point 42 via another strip conductor 48. Furthermore, the first electrode 30 of the reference probe 14 is shown, which is disposed in the same layer 28 (FIG. 1) as the electrode 22. The electrode 30 is likewise connected to the contact point 42 via a strip conductor 50. The not yet contacted contact points 38 and 40 are furthermore provided on the base substrate 16. The diffusion barriers 18, the electrodes 22 and 30, as well as the strip conductors 46, 48, and 50 can each be mounted on the base substrate 16 in subsequent steps by means of the screen printing process. In intermediate steps, both the diffusion barriers 18 and the electrodes 22 or 30 with their connection strip conductors 46, 48 or 50 are respectively embedded within the layers 28 (FIG. 1) of the base substrate 16, that is, enclosed in the plane.

The solid electrolytes 26 and 34 are mounted in a subsequent step of the process shown in FIG. 3b. In this case, the solid electrolytes 24 are placed on the electrodes 22 and the solid electrolyte 34 is placed on the electrode 30. Both the solid electrolytes 26 and the solid electrolyte 34 are embodied as solid electrolyte islands 36, that is, these are not applied over a large area, but only over certain regions which are limited to the region of the electrodes 22 or 30. The region between the solid electrolytes 26 and 34 is filled in with another layer 28 of the base substrate 16, as shown in FIG. 3c. This achieves the embodiment of the solid electrolytes 36, which are disposed virtually in one plane in the corresponding layer 28 of the base substrate 16. This results in that, because of the small-area embodiment of the solid electrolytes 26 or 34, the absolute values of the heat-induced expansion differences between the solid electrolytes 26 and 34 or the base substrate 16 are minimized when there is an operation-induced heating of the entire measuring sensor 10 and therefore of the solid electrolytes 26 and 34 or of the base substrate 16 which have different heat expansion coefficients. As a result, the thermal stresses inside the measuring sensor 10 are reduced so that a formation of cracks in the solid electrolytes 26 or 34 can be prevented.

In a subsequent step of the process shown in FIG. 3d, another layer 28 of the base substrate 16 is mounted on the structure produced prior to this. The layer 28 is comprised of a masking 52, which corresponds to the later disposition of the electrodes 24 or 32. The masking 52 likewise contains the embodiment of the diffusion hole 20. At this point, the electrodes 24 and 32 are mounted in a subsequent step of the process shown in FIG. 3e. Here, the electrodes 24 are again disposed in a circle in accordance with the disposition of the electrodes 22. The electrodes 24 are connected to one another by means of a strip conductor 54 and are connected to the contact point 40 by a further strip conductor 56. The electrode 32 is connected to the contact point 38 via a strip conductor 58. The electrodes 24 and 32 and the strip conductors 54, 56, 58 can again be applied by screen printing.

The measuring sensor 10 as a whole is characterized by a simple, layered construction which can be achieved using generally known and reliably controllable, successive screen printing steps. In particular, the separated construction of the measuring probe 12 and the reference probe 14 in a common base substrate 16 can thus be achieved, wherein the solid electrolytes 26 or 34 can be kept small in relation to the base substrate 16.

The material specifications indicated in the exemplary embodiment are merely examples and can be substituted by any other material suited to the employment purpose of the measuring sensor 10.

What is claimed is:

1. A measuring sensor for determining oxygen content in a gas mixture including exhaust gases of infernal combustion engines, comprising:

a base substrate which is comprised of a base material and which is electrically insulating; and an electrochemical measuring probe and an electrochemical reference probe arranged separate from each other on the base substrate, wherein the electrochemical measuring probe is comprised of:
(a) a diffusion barrier provided on the base substrate;
(b) at least one internal electrode provided on the diffusion barrier;
(c) a solid electrolyte provided as at least one solid electrolyte island on respective ones of the at least one internal electrode; and
(d) at least one external electrode provided on respective ones of the solid electrolyte islands, wherein the electrochemical reference probe is comprised of:
(a') a base material layer comprised of a base material which is the same as the base material of the base substrate and which is provided on the base substrate;
(b') an internal electrode provided on the base material layer and in the same plane as that of the at least one internal electrode of the electrochemical measuring probe;
(c') a solid electrolyte provided on the internal electrode and in the same plane as that of the solid electrolyte of the electrochemical measuring probe; and
(d') an external electrode provided on the solid electrolyte and in the same plane as that of the at least one external electrode of the electrochemical measuring probe, wherein further base material layers comprised of a base material which is the same as the base material of the base substrate are provided around, and in the same respective planes as, the diffusion barrier, the at least one internal electrodes of the electrochemical measuring probe, the internal electrode of the electrochemical reference probe, the solid electrolyte islands of the electrochemical measuring probe, and the solid electrolyte of the electrochemical reference probe, so as to embed at least the diffusion barrier, the at least one internal electrodes for the electrochemical measuring probe, and the internal electrode of the electrochemical reference probe, and wherein a diffusion hole is defined between the electrochemical measuring probe and the electrochemical reference probe which extends from the base substrate through the diffusion barrier and respective base material layers, and out to the gas mixture to be measured.

2. The measuring sensor according to claim 1,
wherein the electrochemical measuring probe is structured to function as a pump cell, and
wherein the electrochemical reference probe is structured to function as a lambda probe.

3. The measuring sensor according to claim 1, wherein embedment by providing further base material layers around, and in the same respective planes as, at least the diffusion barrier, the at least one internal electrodes for the electrochemical measuring probe, and the internal electrode of the electrochemical reference probe encloses same.

4. The measuring sensor according to claim 1, wherein the measuring sensor is constructed of a plurality of individual layers which are applied to the base substrate using screen printing.

5. The measuring sensor according to claim 1, wherein the diffusion barrier of the electrochemical measuring probe is disposed in a first layer.

6. The measuring sensor according to claim 1, wherein the at least one internal electrode of the electrochemical measuring probe and the internal electrode of the electrochemical reference probe are disposed in a second layer.

7. The measuring sensor according to claim 1, wherein the solid electrolyte of the electrochemical measuring probe and solid electrolyte of the electrochemical reference probe are disposed in a third layer.

8. The measuring sensor according to claim 1, wherein the at least one external electrode of the electrochemical measuring probe and the external electrode of the electrochemical reference probe are disposed in a fourth layer.

9. The measuring sensor according to claim 1,
wherein the diffusion barrier, the at least one internal electrode of the electrochemical measuring probe, the internal electrode of the electrochemical reference probe, the solid electrolyte of the electrochemical measuring probe and the electrochemical reference probe, the at least one external electrode of the electrochemical measuring probe, and the external electrode of the electrochemical reference probe are comprised of segments arranged in a circular configuration and spaced apart from each other, and wherein the at least one internal electrode of the electrochemical measuring probe are connected to each other via strip conductor and the at least one external electrode of the electrochemical measuring probe are connected to each other via a strip conductor.

10. The measuring sensor according to claim 9, wherein the respective segments are each disposed offset from each other at an angle of 90°.

11. The measuring sensor according to claim 9, wherein the respective segments are disposed around the diffusion hole which connects the diffusion barrier to the gas mixture.

12. The measuring sensor according to claim 1,
wherein the diffusion barrier, the at least one internal electrode, the solid electrolyte, and the at least one external electrode of the electrochemical measuring probe each has three segments disposed in a circular configuration in one plane and offset from one another by 90°, and wherein the base material layer, the internal electrode; the solid electrolyte, and the external electrode of the electrochemical reference probe each has one segment disposed in a circular configuration with respect to respective segments of the electrochemical measuring probe in one plane and offset from one another by 90°.

* * * * *